United States Patent
Zhu et al.

(10) Patent No.: US 11,564,613 B2
(45) Date of Patent: Jan. 31, 2023

(54) NON-INVASIVE CONTINUOUS HEART RHYTHM MONITORING BASED ON WEARABLE SENSORS

(71) Applicants: SAMSUNG ELECTRONICS CO., LTD., Gyeonggi-Do (KR); The Regents of the University of California, Oakland, CA (US)

(72) Inventors: Li Zhu, Milpitas, CA (US); Viswam Nathan, Mountain View, CA (US); Md Mahbubur Rahman, San Jose, CA (US); Jilong Kuang, San Jose, CA (US); Jeong Woo Kim, San Ramon, CA (US); Jun Gao, Menlo Park, CA (US); David W. Mortara, Milwaukee, WI (US); Jeffrey E. Olgin, Larkspur, CA (US)

(73) Assignees: SAMSUNG ELECTRONICS CO., LTD., Gyeonggi-Do (KR); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 224 days.

(21) Appl. No.: 17/124,438

(22) Filed: Dec. 16, 2020

(65) Prior Publication Data
US 2022/0183608 A1 Jun. 16, 2022

(51) Int. Cl.
  *A61B 5/361* (2021.01)
  *A61B 5/364* (2021.01)
  *A61B 5/00* (2006.01)

(52) U.S. Cl.
  CPC .............. *A61B 5/361* (2021.01); *A61B 5/364* (2021.01); *A61B 5/7203* (2013.01); *A61B 5/6801* (2013.01)

(58) Field of Classification Search
None
See application file for complete search history.

(56) References Cited

U.S. PATENT DOCUMENTS 5,713,367 A * 2/1998 Arnold ................. A61B 5/0535
  600/517
6,067,467 A * 5/2000 John ..................... A61B 5/4821
  600/544

(Continued)

OTHER PUBLICATIONS

Ramesh et al., "Atrial Fibrillation Classification with Smart Wearables Using Short-term Heart Variability and Deep Convolutional Neural Networks," Sensors (Basel, Switzerland), 21(21), 7233, pp. 1-12, Oct. 30, 2021 (Year: 2021).*

(Continued)

*Primary Examiner* — Kennedy Schaetzle
(74) *Attorney, Agent, or Firm* — Cuenot, Forsythe & Kim, LLC

(57) ABSTRACT

Continuously monitoring heart rhythm can include grouping, using computer hardware, a plurality of inter-beat intervals (IBI) data for a user into a plurality of epochs, wherein each epoch includes a subset of the IBI data corresponding to a predetermined time span. For each epoch, a selected feature set selected from a plurality of feature sets is extracted based on a determination of temporal consistency of the epoch. A plurality of epoch classifications may be generated for the epochs using a selected feature processor, wherein each epoch classification indicates whether arrhythmia is detected for the epoch from which the epoch classification is generated. The selected feature processor is selected from a plurality of different feature processors on a per-epoch basis based on the selected feature set extracted from the epoch. An indication of arrhythmia may be output, via an output device of the computer hardware, based on the epoch classifications.

20 Claims, 8 Drawing Sheets

(56) References Cited

U.S. PATENT DOCUMENTS

| | | | |
|---|---|---|---|
| 10,098,561 | B2 | 10/2018 | Brockway et al. |
| 10,332,379 | B2 | 6/2019 | Fahey |
| 10,638,941 | B2 | 5/2020 | Albert et al. |
| 10,750,960 | B2 | 8/2020 | Miao et al. |
| 2003/0052775 | A1* | 3/2003 | Shambroom ............ A61B 5/30 600/300 |
| 2015/0223711 | A1 | 8/2015 | Raeder et al. |
| 2017/0281034 | A1* | 10/2017 | Higgins ................. A61B 5/352 |
| 2019/0076031 | A1 | 3/2019 | Valys et al. |
| 2019/0313947 | A1 | 10/2019 | Li et al. |
| 2020/0100693 | A1 | 4/2020 | Velo |
| 2020/0138306 | A1* | 5/2020 | Li ........................ A61B 5/7267 |
| 2020/0357519 | A1* | 11/2020 | Chakravarthy ...... A61B 5/7267 |
| 2022/0280774 | A1* | 9/2022 | Kim ..................... A61N 1/0484 |

OTHER PUBLICATIONS

Dewar, R. I. et al., "Identification, diagnosis and assessment of atrial fibrillation." Heart, vol. 93, No. 1, Jan. 2007, pp. 25-28.

"Atrial Fibrillation," [online] Centers for Disease Control and Prevention, U.S. Department of Health & Human Services, retreived Sep. 9, 2020, retrieved from the Internet: <https://www.cdc.gov/heartdisease/atrial_fibrillation.htm>, 4 pg.

Camm, J., "Anticoagulation in the Post-Warfarin Era: Where Are We Today?" Camm J. Am J Med 2013, retrieved Dec. 16, 2020, retrieved from the Internet: <http://webedcafe.com/extern/program_media/amjmed.com/2013/anticoag3/figure.php?speaker=camm&figure=26>, 1 pg.

January, C. T., et al. "2014 AHA/ACC/HRS Guidelines for the Management of Patients with Atrial Fibrillation," Circulation, vol. 130, No. 23, Dec. 2, 2014, pp. e199-e267.

Chen, L. Y., et al. "Atrial fibrillation burden: moving beyond atrial fibrillation as a binary entity: a scientific statement from the American Heart Association." Circulation, vol. 137, No. 20, May 15, 2018, pp. e623-e644.

"Learn More about AFib during American Heart Month," [online] The Alliance for Aging Research, Feb. 6, 2015, retrieved from the Internet: <https://www.agingresearch.org/learn-more-about-afib-during-american-heart-month/>, 4 pg.

"CHA2DS2-VASc score," [online] From Wikipedia, the free encyclopedia, retrieved Dec. 16, 2020, retrieved from the Internet: <https://en.wikipedia.org/wiki/CHA2DS2-VASc_score>, 8 pg.

Perez, M.V., et al. "Large-Scale Assessment of a Smartwatch to Identify Atrial Fibrillation." New England Journal of Medicine, vol. 381, No. 20, Nov. 14, 2019, pp. 1909-1917.

"Johnson & Johnson Launches Heartline™, the First-of-its-Kind, Virtual Study Designed to Explore if a New iPhone App and Apple Watch Can Help Reduce the Risk of Stroke," [online] Johnson & Johnson Services, Inc. © 1997-2020, Feb. 25, 2020, retrieived from the Internet: <https://www.jnj.com/johnson-johnson-launches-heartline-the-first-of-its-kind-virtual-study-designed-to-explore-if-a-new-iphone-app-and-apple-watch-can-help-reduce-the-risk-of-stroke>, 4 pg.

"Fitbit Announces Large-Scale Study to Identify Atrial Fibrillation," [online] Fitbit Inc. © 2017, retrieved Dec. 16, 2020, retrieved from the Internet: <https://investor.fitbit.com/press/press-releases/press-release-details/2020/Fitbit-Announces-Large-Scale-Study-to-Identify-Atrial-Fibrillation/default.aspx#:~:text=Fitbit%20wearables%20have%20the%20unique,including%20when%20users%20are%20asleep>, 4 pg.

Park, J. et al., "Atrial fibrillation detection by heart rate variability in Poincare plot," Biomedical Engineering OnLine, vol. 8, No. 38, Dec. 11, 2009, 12 pg.

* cited by examiner

300

| Modules / Scenarios | | 1 | 2 | 3 | 4 |
|---|---|---|---|---|---|
| Blood Pulse Artifacts Detector (BD) | 0: Acceptable (flag not set) 1: Not acceptable (flag set) | 1 | 0 | | |
| IBI Abnormality Detector (ID) | 0: Acceptable (flag not set) 1: Not acceptable (flag set) | X | 0 | 1 | |
| Motion Assessor (MA) | 0: No motion (flag not set) 1: Motion (flag set) | X | X | 0 | 1 |
| Decisions | | D | K | K | D |

1200

Grouping a plurality of inter-beat intervals (IBI) data for a user into a plurality of epochs, wherein each epoch includes a subset of the IBI data corresponding to a predetermined time span
1202

For each of the plurality of epochs, extract a first feature set or a second feature set from the epoch based on a determination of temporal consistency for the epoch
1204

Generate a plurality of epoch classifications for the plurality of epochs using a selected feature processor, each epoch classification indicating presence of arrhythmia for the corresponding epoch, wherein the selected feature processor is selected from a plurality of different feature processors on a per-epoch basis based on the feature set extracted from the epoch
1206

Outputting, via an output device, an indication of arrhythmia based on the plurality of epoch classifications
1208

FIG. 12

NON-INVASIVE CONTINUOUS HEART RHYTHM MONITORING BASED ON WEARABLE SENSORS

TECHNICAL FIELD

This disclosure relates to continuously monitoring heart rhythm and, more particularly, to monitoring heart rhythm non-invasively using wearable sensors to detect arrhythmia in users.

BACKGROUND

Heart arrhythmia refers to a condition in which the heart beats too slowly, too fast, or in an irregular manner. Atrial Fibrillation (AFib), being a type of heart arrhythmia, is a condition in which the upper chambers of the heart, referred to as the Atria, beat irregularly. The irregular beating of the Atria results in poor blood flow to the lower chambers of the heart referred to as the ventricles. In AFib, the atria and the ventricles beat in an uncoordinated manner and the chaotic depolarization (activation of the atria) causes the heart to beat irregularly. Sometimes AFib is also accompanied by beating too slow (bradycardia) or too fast (AFib with rapid ventricular response).

Detection of AFib can be difficult as may persons suffering from the condition are asymptomatic. Further complicating detection, AFib may occur intermittently. Detection of AFib, however, is a significant issue as AFib has been associated with higher incidence of stroke and heart failure and higher risk of mortality. The Center for Disease Control has estimated that between 2.7 and 6.1 million people in the United States suffer from AFib. This number is expected to grow as the population continues to age.

Keeping a patient in a clinical setting to detect what may be an intermittent condition is also not a practical solution. Unfortunately, monitoring heart rhythm in an accurate manner outside of a clinical setting poses numerous technological challenges. As such, AFib may go undiagnosed until the condition causes a life-threatening condition. Since AFib is progressive in nature, early detection is an important aspect of managing the condition.

SUMMARY

In one aspect, a method for continuous heart rhythm monitoring can include grouping, using computer hardware, a plurality of inter-beat intervals (IBI) data for a user into a plurality of epochs, wherein each epoch includes a subset of the IBI data corresponding to a predetermined time span and, for each of the plurality of epochs, extracting, from the epoch, a selected feature set selected from a plurality of feature sets based on a determination of temporal consistency of the epoch. The method can include generating a plurality of epoch classifications for the plurality of epochs using a selected feature processor, each epoch classification indicating whether arrhythmia is detected for the epoch from which the epoch classification is generated, wherein the selected feature processor is selected from a plurality of different feature processors on a per-epoch basis based on the selected feature set extracted from the epoch. The method also can include outputting, via an output device of the computer hardware, an indication of arrhythmia based on the plurality of epoch classifications.

In another aspect, a system for continuous heart rhythm monitoring can include a processor programmed to initiate operations. The operations can include grouping a plurality of IBI data for a user into a plurality of epochs, wherein each epoch includes a subset of the IBI data corresponding to a predetermined time span and, for each of the plurality of epochs, extracting, from the epoch, a selected feature set selected from a plurality of feature sets based on a determination of temporal consistency of the epoch. The operations can include generating a plurality of epoch classifications for the plurality of epochs using a selected feature processor, each epoch classification indicating whether arrhythmia is detected for the epoch from which the epoch classification is generated, wherein the selected feature processor is selected from a plurality of different feature processors on a per-epoch basis based on the selected feature set extracted from the epoch. The operations also can include outputting, via an output device of the system, an indication of arrhythmia based on the plurality of epoch classifications.

In another aspect, a computer program product includes one or more computer readable storage media, and program instructions collectively stored on the one or more computer readable storage media. The program instructions are executable by computer hardware to initiate operations including grouping a plurality of IBI data for a user into a plurality of epochs, wherein each epoch includes a subset of the IBI data corresponding to a predetermined time span and, for each of the plurality of epochs, extracting, from the epoch, a selected feature set selected from a plurality of feature sets based on a determination of temporal consistency of the epoch. The operations can include generating a plurality of epoch classifications for the plurality of epochs using a selected feature processor, each epoch classification indicating whether arrhythmia is detected for the epoch from which the epoch classification is generated, wherein the selected feature processor is selected from a plurality of different feature processors on a per-epoch basis based on the selected feature set extracted from the epoch. The operations also can include outputting, via an output device of the computer hardware, an indication of arrhythmia based on the plurality of epoch classifications.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more example implementations; however, the accompanying drawings should not be taken to limit the invention to only the examples shown. Various aspects and advantages will become apparent upon review of the following detailed description and upon reference to the drawings.

FIG. 12 illustrates an example method of detecting arrhythmia in a user using the system of FIG. 1.

DETAILED DESCRIPTION

Figure 1:
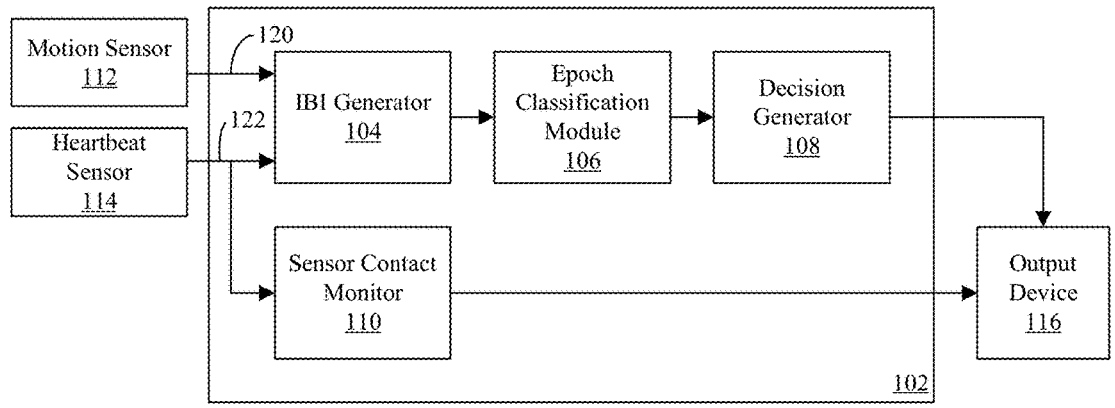
FIG. 1 illustrates an example system capable of detecting arrhythmia in a user.

This disclosure relates to continuously monitoring heart rhythm and, more particularly, to monitoring heart rhythm non-invasively using wearable sensors to detect arrhythmia in users. In accordance with the inventive arrangements described within this disclosure, methods, systems, and computer program products are provided that are capable of detecting Atrial Fibrillation (AFib) in a with a higher degree of accuracy than other available solutions. A system, for example, that incorporates wearable sensors may be used to continuously monitor heart rhythm to accurately detect AFib in a user.

The inventive arrangements described within this disclosure address various technical deficiencies of other available technologies. For example, available technologies for detecting AFib often rely on sensor arrangements that are cumbersome and uncomfortable for the user. This means that the user is unlikely to wear the sensors outside of a clinical setting for the extended periods of time necessary to detect AFib. Given the intermittent nature of AFib, such technologies are less likely to accurately detect AFib in users. A Holter monitor is an example of a sensor arrangement and portable device capable of monitoring electrocardiography (ECG) that may be cumbersome for a user to wear for extended periods of time.

Available technologies for detecting AFib suffer from other technical issues such as an inability to collect sufficient amounts of quality data from which AFib may be detected in the user. Available technologies collect sensor data that include high levels of motion artifacts or noise induced by motion of the user while wearing sensors and performing daily activities outside the clinical setting. These technologies then discard large amounts of noise-ridden sensor data leaving significantly less data from which AFib may be accurately detected. The amount of data that is discarded is often so large that accurate detection of AFib becomes unlikely or impossible particularly given the intermittent nature of AFib in users.

The inventive arrangements described within this disclosure utilize a multi-stage processing architecture for detecting heart arrhythmia and, more particularly, AFib in a user. A first stage of the architecture is capable of operating on raw sensor signals from multiple, different sensors to generate inter-beat intervals (IBI) data. The first stage is capable of assessing the IBI data on a per IBI data item basis such that only those IBI data meeting minimum quality metric(s) are grouped into epochs. A second stage of the architecture is capable of assessing the epochs to determine whether individual ones of the epochs indicate arrhythmia. The second stage is capable of processing the epochs through a feature processor selected from a plurality of different feature processors based on temporal consistency of the epochs. The decision to process an epoch through a particular feature processor is performed on a per epoch basis. A third stage of the architecture evaluates epoch classifications generated by the second stage to determine whether arrhythmia is detected for the user. The third stage is capable of determining whether AFib is detected by evaluating epoch classifications for a plurality of epochs. The third stage is further capable of accounting for one or more user-specific attributes in determining whether AFib is detected for the user.

FIG. 1 illustrates an example system 102 capable of detecting arrhythmia in a user. One type of arrhythmia that system 102 is capable of detecting is AFib. System 102 is capable of operating in real-time to continuously monitor heart rhythm of a user to detect the occurrence of AFib in the user more accurately than other available technologies. The increased accuracy in combination with the ability to operate in real-time over extended periods of time, allows system 102 to more accurately determine AFib burden on the user. AFib burden is the percentage of time that the user spends in AFib per day. AFib burden moves beyond a binary determination of the presence of AFib by providing a non-binary measure of heart arrhythmia that carries important prognostic implications. AFib burden, for example, is associated with higher prevalence and incidence of heart failure and higher risk of mortality.

System 102 may be implemented within an electronic device 100. Electronic device 100 may be a portable device. In an example implementation, electronic device 100 is wearable by a user. An example of a portable device is a portable computing or communication device equipped with, or coupled, to suitable sensors. Examples of electronic device 100 may include, but are not limited to, a mobile (e.g., smart) phone, a smart watch, or both operating in a coordinated manner where the smart watch is communicatively linked with the smart phone. An example implementation of device 100 is described herein in connection with FIG. 13.

System 102 may be implemented in hardware, e.g., as dedicated circuitry; program code executed by one or more processors; or a combination thereof. In an example implementation, system 102 is capable of executing entirely within device 100. That is, system 102 is capable of performing the various operations described within this disclosure without accessing or contacting another system or device external to electronic device 100 such as a server, cloud computing node, or other data processing system. In this regard, system 102 is said to execute locally on device 100.

System 102 includes a plurality of different processing blocks. In the example, system 102 includes an IBI generator 104, an epoch classification module 106, a decision generator 108, and optionally a sensor contact monitor 110. Electronic device 100 also can include a plurality of different types of sensors each capable of generating corresponding sensor signals. In the example, electronic device 100 includes a motion sensor 112 and a heartbeat sensor 114. In other example implementations, motion sensor 112 and heartbeat sensor 114 may be included in system 102.

Motion sensor 112 may be implemented as an inertial measurement unit (IMU). An IMU is an electronic sensor that is capable of measuring and outputting sensor signals that indicate a body's specific force, angular rate, and sometimes the orientation of the body, using a combination of accelerometers, gyroscopes, and, in some cases, magnetometers. Heartbeat sensor 114 may be implemented as any of a variety of sensors capable of detecting heartbeat of a user and from which IBI data may be generated. Examples of heartbeat sensors 114 include, but are not limited to, a photoplethysmography (PPG) sensor, an electrocardiogram (ECG) device/sensor, a finger temperature sensor, a skin conductance sensor, and a respiration rate sensor. In this regard, while PPG sensors and PPG signals are used from time-to-time within this disclosure for purposes of illustration, in other example implementations, other varieties of heartbeat sensors and corresponding signals, including those example sensors mentioned herein, from which IBI data may be generated may be used in place of a PPG sensor to implement heartbeat sensor 114.

In an example where heartbeat sensor 114 is implemented as a PPG sensor, the PPG sensor may be implemented to include one or more light sources and corresponding photodetector(s). The light source of the PPG sensor may be a light emitting diode or "LED" such as an infrared LED, a green LED, or a plurality of different colored LEDs. The light source emits light to tissue of the user and the photodetector measures the reflected light from the tissue with the reflected light being proportional to blood volume variations.

Motion sensor 112 and heartbeat sensor 114 may be implemented as wearable sensors. In the example of FIG. 1, motion sensor 112 and heartbeat sensor 114 both are included in electronic device 100. In another example implementation, one of motion sensor 112 or heartbeat sensor 114 may be included in electronic device 100 while the other one of sensors 112 or 114 is included in a different device communicatively linked to electronic device 100 via a wired or wireless communication link. In still another example implementation, both motion sensor 112 and heartbeat sensor 114 may be separate from electronic device 100 and coupled to electronic device 100 via wired or wireless communication links. Accordingly, whether independent of electronic device 100 or incorporated into electronic device 100, which may be worn and/or carried by the user, both motion sensor 112 and heartbeat sensor 114 convey sensor data concurrently and for a particular user. The sensor implementations described are provided for purposes of illustration. It should be appreciated that such sensors may be augmented with additional circuitry and/or functionality. Further, electronic device 100 may include additional sensors not described in the example of FIG. 1.

IBI generator 104 is capable of receiving motion signals 120 generated by motion sensor 112 and heartbeat signals 122 generated by heartbeat sensor 114. In general, IBI generator 104 is capable of capturing the IBI values, referred to herein as IBI data, of the continuous heartbeat signal 122. IBI generator 104 is also capable of determining the reliability or quality of each individual IBI value. A single IBI data item including an IBI value is referred to as an IBI datum. IBI generator 104 is capable of determining the reliability of each IBI datum based on an analysis of motion signals 120 and heartbeat signals 122 corresponding in time to each respective IBI datum. IBI generator 104 further is capable of outputting the IBI data organized or grouped into epochs. An epoch is a predetermined time span that includes one or more IBI data. As an example, an epoch may be a time span of 30 seconds, 40 seconds, 50 seconds, or 1 minute. For a user with a heart rate of 60 beats per minute, an epoch that is 1 minute in length will include 60 IBI data (e.g., 60 IBI values). Epochs generated by IBI generator 104 are provided to epoch classification module 106. An example implementation of IBI generator 104 is described herein in connection with FIG. 2.

Epoch classification module 106 performs analysis on a per-epoch basis. Each epoch may be classified as one that is indicative of AFib or one that is not indicative of AFib. Epoch classification module 106 is capable of processing the epochs through a selected one of a plurality of different signal processing channels. The particular signal processing channel through which an epoch is processed is selected based on one or more attributes of the epoch that are indicative of temporal consistency of the epoch. In general, temporal consistency, to be described herein in greater detail, is derived from the amount of real-world motion artifact noise affecting the IBI data of the epoch. Each signal processing channel is capable of generating an epoch classification for the epoch that is processed. The signal processing channel may be selected on a per-epoch basis.

The signal processing performed by epoch classification module 106 mitigates consequences of discarding noisy data thereby enabling and improving the accuracy of detecting AFib in the user and the accuracy of determining AFib burden on the user. That is, epoch classification module 106 is capable of operating on a larger amount of data than other available technologies thereby increasing the time that the user is monitored and increasing the accuracy of AFib detection. Epoch classifications generated by epoch classification module 106 are provided to decision generator 108. An example implementation of epoch classification module 106 is described herein in connection with FIG. 5.

Decision generator 108 is capable of determining whether the user has, or is, suffering from, AFib based on the epoch classifications received from epoch classification module 106. In another example implementation, decision generator 108 is capable of calculating AFib burden on the user based on the AFib detections and epoch classifications received from epoch classification module 106. Whereas epoch classifications cover a limited period of time, decision generator 108 is capable of making a determination as to whether the user has or is suffering an AFib attack based on a plurality of consecutive epochs.

In one or more example implementations, decision generator 108 may be tuned or biased to account for various user-specific attributes. Operation of decision generator 108 may be controlled based on the user-specific attributes provided thereto. Accordingly, decision generator 108 is capable of balancing the amount of data used to make determinations with accuracy of AFib detection. An example implementation of decision generator 108 is described herein in connection with FIG. 6.

Sensor contact monitor 110 may be optionally included. Sensor contact monitor 110 is capable of monitoring heartbeat signals 122 to determine whether such signals are reliable. In response to determining that heartbeat signals 122, e.g., a portion of heartbeat signals 122 corresponding to a particular time span or window, are not reliable, sensor contact monitor 110 is capable of outputting feedback to the user via output device 116 of electronic device 100 thereby notifying the user of the low quality of heartbeat signals 122. The notification provided by sensor contact monitor 110 may be augmented to include instructions for correcting the problem to improve the quality of heartbeat signals 122.

In one aspect, the instructions may be specific to the type of abnormality or issue detected in heartbeat signals 122. Sensor contact monitor 110 ensures that quality heartbeat signals 122 are obtained while providing the user with feedback as to whether heartbeat sensor 114 is worn correctly. The instructions may be particularized to the specific type of heartbeat sensor 114 that is used. For example, the instructions may differ based on whether heartrate sensor 114 is implemented as a PPG sensor, a finger temperature sensor, a skin conductance sensor, or a respiration rate sensor. Further, the instructions may vary based on the type of apparatus or mechanism used to couple or fasten the sensor to the user (e.g., a wristband, strap, etc.). In this regard, sensor contact monitor 110 is operative to reduce the effects of noise on heartbeat signals 122 and increase the amount of usable data derived from heartbeat signals 122 that may be used for purposes of detecting AFib in the user. In one or more other example implementations, sensor contact monitor 110 receives motion signals 120 generated by motion sensor 112 and uses motion signals 120 in combination with heartbeat signals 122 to determine whether heartbeat signals 122 are unreliable. An example implementation of sensor contact monitor 110 is described herein in connection with FIG. 8.

Figure 2:
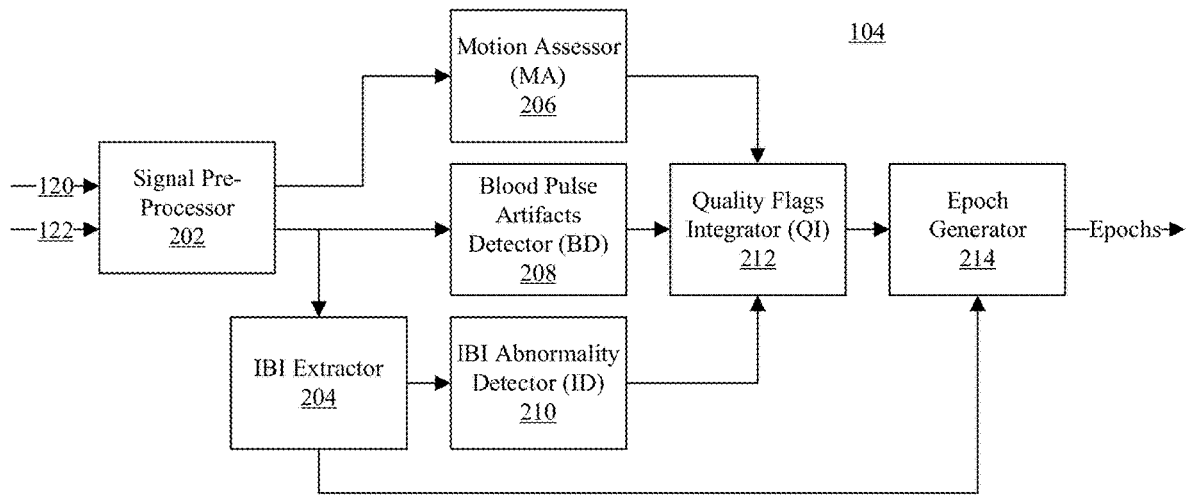
FIG. 2 illustrates an example implementation of an inter-beat intervals (IBI) generator described in connection with FIG. 1.

FIG. 2 illustrates an example implementation of IBI generator 104 of FIG. 1. FIG. 2 illustrates example processing performed by IBI generator 104 on motion signals 120 and heartbeat signals 122 to generate epochs including one or more IBI data. In the example of FIG. 2, IBI generator 104 includes a signal pre-processor 202, an IBI extractor 204, a motion assessor (MA) 206, a blood pulse artifacts detector (BD) 208, an IBI abnormality detector (ID) 210, a quality flags integrator (QI) 212, and an epoch generator 214.

As noted, motion signals 120 and heartbeat signals 122 may be collected from motion sensor 112 and heartbeat sensor 114 worn by the user. For purposes of discussion, motion signals 120 and heartbeat signals 122 each may be provided to signal pre-processor 202 as a data stream of sampled values having been sampled at a particular sampling rate by each respective sensor. In one aspect, signal pre-processor 202 is capable of receiving motion signals 120 and the heartbeat signals 122 and resampling one or both of motion signals 120 and heartbeat signals 122 so that both have a same or common sampling rate. Signal pre-processor 202 is also capable of time aligning motion signals 120 with the heartbeat signals 122. Time aligning motion signals 120 and heartbeat signals 122 ensures that analysis performed on the signals and/or resulting data is time aligned and corresponds to the same period of time (e.g., a same IBI datum).

In another example implementation, signal pre-processor 202 also is capable of performing one or more filter operations on received sensor signals. For example, signal pre-processor 202 is capable of band-pass filtering and normalizing heartbeat signals 122. These operations remove baseline wandering and high frequency noise from heartbeat signals 122. In an example implementation, signal pre-processor 202 is also capable of performing one or more filter operations on motion signals 120.

Signal pre-processor 202 is capable of outputting the resulting motion signals to MA 206 and the resulting heartbeat signals to both BD 208 and IBI extractor 204. IBI extractor 204 is capable of analyzing the heartbeat signals subsequent to processing by signal pre-processor 202 and detecting peaks of blood volume in the heartbeat signals to generate IBI values. Each individual IBI datum, for example, includes a measure of time between a pair of consecutively detected peaks in blood volume corresponding to heart beats of the user (e.g., an IBI value). Each IBI datum may other data such as a time stamp or other time information corresponding to one or both of the peaks defining the IBI value.

In the example of FIG. 2, each of MA 206, BD 208, and ID 210 is capable of operating in a synchronized manner. IBI extractor 204 generates a plurality of IBI data, where each IBI datum represents a particular time span. The time span of an IBI datum is the time from one peak of the heartbeat signal to a next consecutive peak of the heartbeat signal. As ID 210 operates on a selected IBI datum, MA 206 operates on the motion signals that correspond to, e.g., are within, the time span covered by the selected IBI datum. Similarly, BD operates on the heartbeat signals that correspond to, e.g., are within, the time span covered by the selected IBI datum. Each of MA 206 and BD 208 outputs a result, e.g., a flag, that is correlated and associated with the selected IBI datum and assessment performed by ID 210. QI 212 is able to assess the quality of each individual IBI datum based on the combination of results generated for the selected IBI datum. That is, for each IBI datum, QI 212 is capable of assessing quality of the IBI datum based on results generated by MA 206, BD 208, and ID 210.

MA 206 is capable of analyzing the motion signals to detect instances where the motion signals indicate an amount of motion or movement of the user that exceeds a pre-determined motion threshold for time spans corresponding to individual ones of IBI data. For motion signals corresponding to a time span of an IBI datum currently being processed, MA 206 is capable of flagging portions of the motion signal that indicate a level of motion by the user that exceeds the motion threshold. In an example implementation, MA 206 is capable of flagging each motion signal sample in the time span of the IBI datum being processed that exceeds the motion threshold. Those motion signal samples not exceeding the motion threshold are not flagged.

In an example implementation, MA 206 is capable of determining the local power of the received motion signal against the baseline power of the motion signal. For example, MA 206 is capable of determining the local power using a window that is small or narrow in time compared to the window used to calculate the baseline power of the motion signal. In general, IBI values are sensitive to abrupt activity of the user, while being insensitive to baseline gentle movement. MA 206 is capable of flagging motion signal samples used to compute the local power in response to the local power divided by the baseline power exceeding a power threshold. As an illustrative and non-limiting example, the window sizes may be fixed parameters where local power is determined using a 1 second time window while baseline power is determined using a 10 second time window. The time window values provided are for purposes of illustration and may be larger or smaller than noted. In other example implementations, the size of the windows may depend on IBI value(s) and/or epoch length.

BD 208 is capable of analyzing the heartbeat signals to detect noise within the signals. BD 208, for example, is capable of detecting noisy PPG samples that indicate spikes or discontinuities in the heartbeat signals. Spikes and/or discontinuities in the heartbeat signals are often caused by sudden misplacement or shifting movement of heartbeat sensor 114 relative to the user. In one aspect, for a given time span corresponding to an IBI datum currently being processed, BD 208 is capable of removing baseline wander from heartbeat signals. Baseline wander is a low frequency artifact within the heartbeat signals. While any of a variety of available baseline wander removal techniques may be used, in one aspect, BD 208 uses a high-pass filter to remove baseline wander from the heartbeat signals. Having removed baseline wander, sudden changes on the heartbeat signals are likely sparse and are unlikely to significantly alter the distribution of amplitude of PPG samples. In another aspect, BD 208 is capable of detecting spikes and/or discontinuities in heartbeat signals by comparing the local amplitude range of PPG samples against the standard deviation of the heartbeat signal with the baseline wander removed. In an example implementation, BD 208 is capable of flagging each heartbeat signal sample in the time span of the IBI datum being processed that exceeds a threshold value. Those heartbeat signal samples in the time span that do not exceed the threshold value are not flagged. The processing implemented by BD 208 is capable of detecting noise types such as a sudden spike or step on the heartbeat signal and flagging such instances of noise as such types of noise types are more likely to adversely affect decision accuracy.

ID 210 is capable of evaluating reliability of IBI data based on temporal dynamics of the IBI data sequence. For example, ID 210 is capable of detecting differences between consecutive IBI values (e.g., the time span specified by a first IBI datum followed by a second consecutive IBI datum) that exceed a threshold. ID 210 is capable of flagging an IBI datum that varies from the previous IBI datum by more than a predetermined variability threshold. In general, ID 210 determines that a given IBI datum is not reliable and is flagged based on detecting a variance as noted, where the variance is presumed to be due to abnormal heart rhythm or motion artifacts. In an example implementation, ID 210 is capable of flagging each IBI datum having a variability that exceeds the variability threshold.

QI 212 is capable of receiving the output from each of MA 206 (e.g., an MA flag), BD 208 (e.g., a BD flag), and ID 210 (e.g., IBI datum and ID flag) corresponding to a given IBI datum and providing the IBI datum with the corresponding flag(s), if any, to epoch generator 214. In one aspect, for each IBI datum, QI 212 is capable of combining the various flags for the IBI datum, if any, and the IBI datum itself into a data structure that is provided to epoch generator 214. Epoch generator 214 is capable of grouping IBI data into epochs of a predetermined time span. Epoch generator 214, in generating epochs, includes only those IBI data that meet minimum quality requirements based on the flag(s) associated with each respective IBI datum.

In an example implementation, epoch generator 214 is capable of keeping and discarding IBI data for purposes of generating epochs as follows:

Epoch generator 214 discards each IBI datum having the BD flag set regardless of the state of the ID and MA flags;
Epoch generator 214 keeps each IBI datum that does not have the BD flag set, has the ID flag set, and that does not have the MA flag set;
Epoch generator 214 discards each IBI datum that does not have the BD flag set, has the ID flag set, and has the MA flag set; and
Epoch generator 214 keeps keeping each IBI datum that does not have the BD flag set and does not have the ID flag set regardless of the state of the MA flag.

For IBI data with the BD flag set, extracting reliable IBI values is exceedingly difficult. IBI data that are discarded are not included in the epochs generated by epoch generator 214. IBI data that is kept is used by epoch generator 214 in generating epochs. The signal processing performed by IBI generator 104 generally seeks to optimize the trade-off between accuracy and data usage by increasing the amount of analyzable data for purposes of detecting AFib and/or determining AFib burden. This further facilitates arrhythmia and AFib detection and/or AFib determination despite mild body movement on the part of the user.

Figures 3, 4:
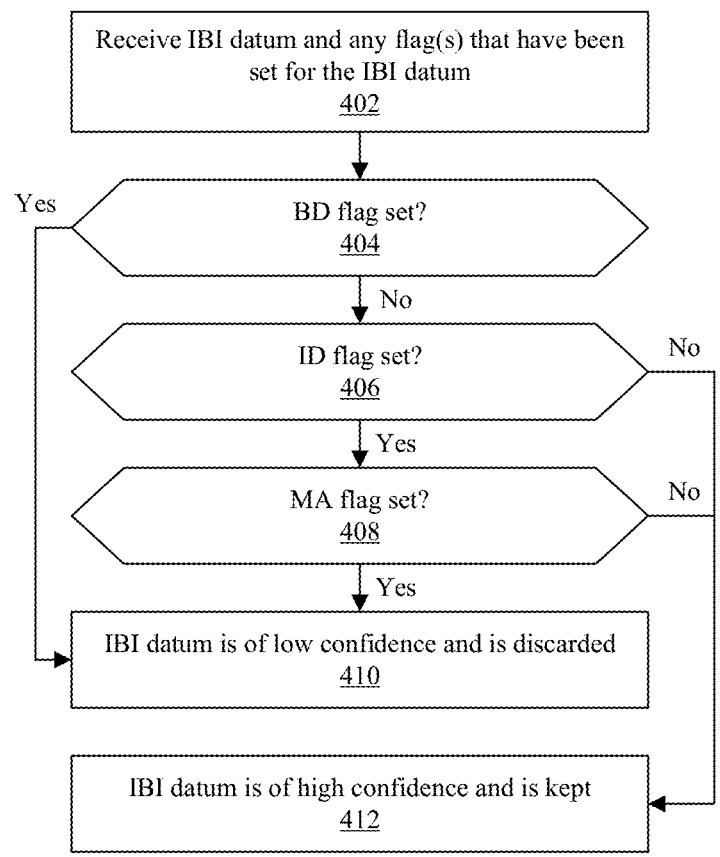
FIG. 3 is a table illustrating example signal processing operations performed by the IBI generator of FIG. 1.
FIG. 4 illustrates an example method depicting certain operative features of the IBI generator of FIG. 1.

FIG. 3 is a table 300 illustrating example signal processing operations performed by IBI generator 104 with respect to keeping and discarding IBI data. Table 300 illustrates the decisions made by IBI generator 104 as to keeping (K) and discarding (D) a given IBI datum based on the state of the flags corresponding to the IBI datum as determined by MA 206, BD 208, and ID 210. In table 300, "X" represents a "don't care" state.

FIG. 4 illustrates an example method 400 depicting certain operative features of IBI generator 104. More particularly, method 400 illustrates certain operative features corresponding to keeping and discarding IBI data performed by epoch generator 214. For purposes of illustration, method 400 illustrates processing of an IBI datum. It should be appreciated that method 400 may iterate as needed to continually process IBI data for purposes of grouping IBI data to form epochs.

In block 402, epoch generator 214 receives an IBI datum along with any flags that have been set for the IBI datum as output from QI 212. In block 404, epoch generator 214 determines whether the BD flag for the IBI datum is set. In response to determining that the BD flag for the IBI datum is set, method 400 continues to block 410 where the IBI datum, being considered a low confidence value, is discarded and not used for epoch generation. In response to determining that the BD flag for the IBI datum is not set, method 400 continues to block 406.

In block 406, epoch generator 214 determines whether the ID flag for the IBI datum is set. In response to determining that the ID flag for the IBI datum is set, method 400 continues to block 408. In response to determining that the ID flag for the IBI datum is not set, method 400 continues to block 412 where the IBI datum, being considered a high confidence value, is kept and is used for epoch generation.

In block 408, epoch generator 214 determines whether the MA flag for the IBI datum is set. In response to determining that the MA flag for the IBI datum is set, method 400 continues to block 410 where the IBI datum, being considered a low confidence value, is discarded and not used for epoch generation. In response to determining that the MA flag for the IBI datum is not set, method 400 continues to block 412 where the IBI datum, being considered a high confidence value, is kept and used for epoch generation. In cases where both the ID flag and MA flag are set for an IBI datum, the IBI datum is determined to be of low quality. In cases where the ID flag is set and the MA flag is not set for the IBI datum, the abnormality detected by ID 210 is determined to have been due to heart rhythm of the user and not noise from excess motion.

Figure 5:
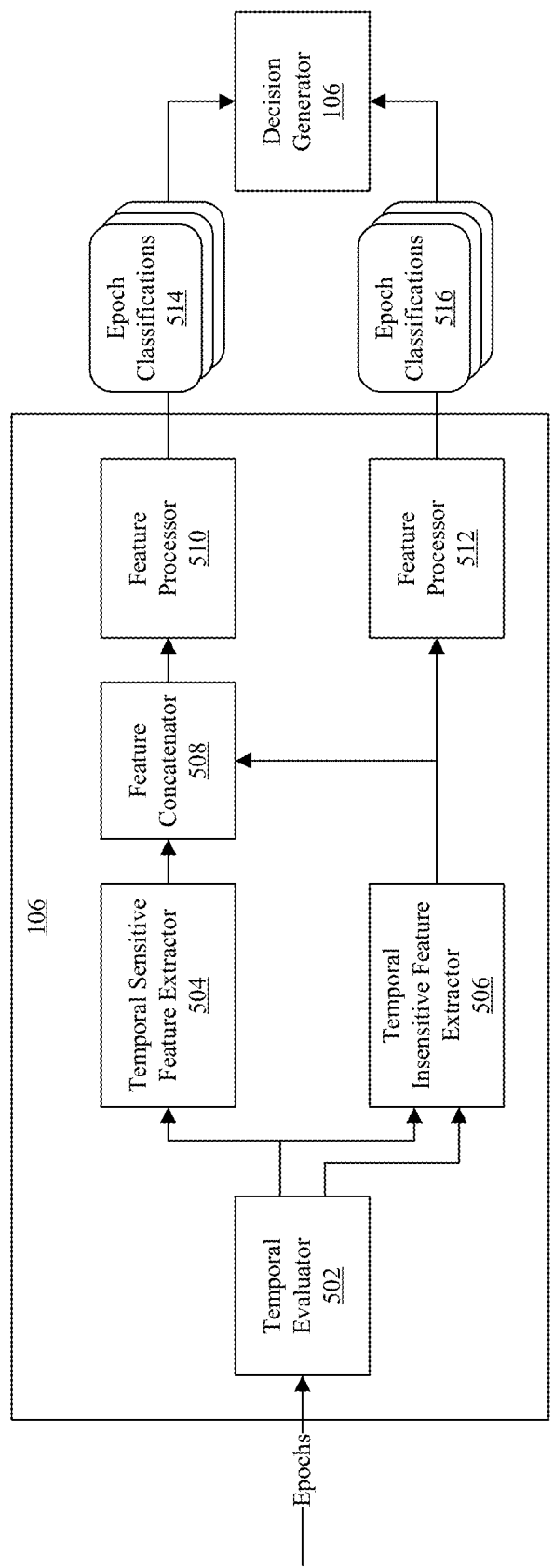
FIG. 5 illustrates an example implementation of an epoch classification module described in connection with FIG. 1.

FIG. 5 illustrates an example implementation of epoch classification module 106 of FIG. 1. In one aspect, epoch classification module 106 implements a dual channel architecture where epochs are processed through different channels based on temporal consistency of each respective epoch. The determination of whether an epoch is temporal consistent or temporal inconsistent depends on the IBI data included in the epoch and may be performed on a per-epoch basis.

In the example of FIG. 5, epoch classification module 106 includes a temporal evaluator 502, a temporal sensitive feature extractor 504, a temporal insensitive feature extractor 506, a feature concatenator 508, a feature processor 510, and a feature processor 512.

Temporal evaluator 502 is capable of receiving epochs generated by IBI generator 104. Temporal evaluator 502 determines, on a per-epoch basis, whether an epoch is temporal consistent or temporal inconsistent. In general, those epochs formed from a set of IBI data where a minimum number of IBI data were discarded by IBI generator 104 leaving one or more gaps in time in the epoch may be considered to be temporal inconsistent. Those epochs formed from a set of IBI data where less than a minimum number of IBI data were discarded or no IBI data were discarded by IBI generator 104 leaving fewer, smaller, or no gaps in time in the epoch may be considered to be temporal consistent.

In one aspect, temporal evaluator 502 is capable of analyzing the IBI data in the received epoch to determine the number of gaps, if any, that exist in the IBI data, the length of each such gap (e.g., the number of IBI data discarded forming the gap), and/or the total length of all gaps in a given epoch. For purposes of temporal consistency evaluation, a gap is formed by discarding an IBI datum or a plurality of IBI data such that the IBI datum remaining at each end of the gap, e.g., bounding the gap, are not temporally consecutive. That is, as created by IBI extractor 204, the IBI datum at one end of the gap was separated from the IBI datum at the other end of the gap by at least one intervening IBI datum (e.g., ordered in time) that, by operation of IBI generator 104, has been discarded.

In an example implementation, temporal evaluator 502 is capable of comparing one or more of the aforementioned criteria (e.g., number of gaps, length of each gap, and total length of all gaps in a given epoch) to corresponding predetermined thresholds on a per epoch basis. In response to determining that any one or more or any combination of the measures exceeds the corresponding threshold, temporal evaluator 502 determines that the epoch is temporal inconsistent. In another example implementation, temporal evaluator 502 is capable of calculating a cost function that depends on one or more or all of the measures noted and determines that the epoch is temporal inconsistent in response to determining that the cost, as determined by the cost function, exceeds a threshold cost. In an example, the cost function may sum the respective measures and optionally apply a weight to each. In another example, the cost function may multiply the number of gaps by the average length of the gaps for the epoch.

Temporal evaluator 502 provides those epochs considered to be temporal consistent to both temporal sensitive feature extractor 504 and to temporal insensitive feature extractor 506. Temporal evaluator 502 provides those epochs considered to be temporal inconsistent only to temporal insensitive feature extractor 506. The temporal gaps in temporal inconsistent epochs preclude temporal sensitive feature extractor 504 from extracting any meaningful features that are temporally sensitive. Thus, temporally intact epochs, in reference to temporal consistent epochs, are provided to both temporal sensitive feature extractor 504 and temporal insensitive feature extractor 506, while those epochs not temporally intact, e.g., temporal inconsistent, are provided only to temporal insensitive feature extractor 506. The determination of temporal consistency for an epoch also determines the particular feature processor 510, 512 to which the epoch is provided for processing.

Temporal sensitive feature extractor 504 is capable of extracting one or more temporal sensitive features from each received epoch. A temporal sensitive feature is a feature that measures a temporal relationship, e.g., changes, between temporally consecutive IBI data. Temporal sensitive features, for example, express or specify temporal dynamics of a temporally consecutive sequence of IBI data. Thus, an epoch must be sufficiently temporal consistent to obtain valid or accurate temporal sensitive features from temporal sensitive feature extractor 504. Examples of temporal sensitive features that may be extracted from a temporal consistent epoch by temporal sensitive feature extractor 504 may include, but are not limited to, mean stepping increment, dispersion against diagnosis, and correlation coefficients of points on a Poincare plot. An example mean stepping increment feature may be determined according to:

$$\text{Mean Stepping} = \frac{\frac{1}{n-2}\sum_{k=1}^{n-2}\sqrt{(I_j - I_{j-1})^2 + (I_{j+1} - I_{j+2})^2}}{\frac{1}{n}\sum_{j=1}^{n} I_j},$$

where $I_1, I_2, \ldots, I_n$ denote consecutive IBI values and n denotes the number of survived IBI values in an epoch. A Poincare plot analysis is a geometrical and nonlinear technique used to assess the dynamics of heart rate variability. In a Poincare plot, each R-R interval (e.g., IBI datum) is plotted as a function of the previous R-R interval where the values of each pair of successive R-R intervals define a point in the plot. Correlation coefficients may be calculated for points on the Poincare plot and extracted as features of the epoch. For example, points on a Poincare plot are formed by pairs of IBI values $(I_j, I_{j-1})$. Dispersion of the distance on a Poincare plot from one IBI datum to a next consecutive IBI datum can be used to make machine-based automated decisions about the likelihood of AFib during a plotted epoch. See, e.g., Park et al., "Atrial fibrillation detection by heart rate variability in Poincare plot," Biomedical Engineering OnLine (Dec. 11, 2009).

Temporal insensitive feature extractor 506 is capable of extracting one or more temporal insensitive features from each received epoch. A temporal insensitive feature measures a characteristic of IBI data that is not dependent on temporally consecutive IBI data. For example, temporal inconsistent features may express or specify statistical distribution of IBI amplitudes. Thus, temporal insensitive feature extractor 506 is capable of extracting temporal insensitive features from epochs that are temporal inconsistent. Examples of temporal insensitive features that may be extracted from a temporal inconsistent epoch by temporal insensitive feature extractor 506 may include, but are not limited to, heart rate variability (HRV), entropy, histogram-based measures, mean, standard deviation, kurtosis, and/or skewness. Entropy may be determined according to: Entropy=$-\Sigma_{i=1}^{n} p_i \cdot \log_2(p_i)$, where p is the probability distribution of IBI values of the IBI data.

For each temporal consistent epoch, temporal insensitive features extracted by temporal insensitive feature extractor 506 and temporal sensitive features extracted by temporal sensitive feature extractor 504 are provided to feature concatenator 508. Feature concatenator 508 joins, or concatenates, both types of features for each temporal consistent epoch and provides the concatenated features to feature processor 510. For each temporal inconsistent epoch, the temporal insensitive features extracted by temporal insensitive feature extractor 506 are provided to feature processor 512.

In an example implementation, each of feature processors 510, 512 may be implemented as a classifier. Feature processor 510 may be pre-trained to classify received epochs as exhibiting AFib or not based on both temporal sensitive features and temporal insensitive features. Feature processor 512 may be pre-trained to classify received epochs as exhibiting AFib or not based on temporal insensitive features (e.g., only temporal insensitive features). Feature processors 510, 512 may be implemented using the same or different machine learning architectures. For example, feature processors 510, 512 may be implemented as convolutional neural networks, recurrent neural networks, support vector machines, random forest, or logistical regression. Still, despite the particular machine learning structure used to implement each of feature processors 510, 512, feature processor 510 is pre-trained on a different feature set than is feature processor 512. Feature processor 510 outputs epoch classifications 514 for temporal consistent epochs. Feature processor 512 outputs epoch classifications 516 for temporal inconsistent epochs. Each epoch classification 514 and 516 specifies whether AFib is detected in the corresponding epoch. Epoch classifications 514 and 516 are provided to decision generator 108.

The dual channel architecture of epoch classification module 106 enables system 102 to detect AFib in epoch, e.g., periods of time, where significant noise from motion artifacts may be present. The channel including feature processor 510 generates epoch classifications during periods of time with little or no noise, while the channel including feature processor 512 generates epoch classifications during periods of time where the level of noise is higher and temporal consistency is not available. Since low temporal consistency generally implies that the signals being processed suffered greater noise and/or interference, feature processor 512 may be configured, e.g., pre-trained, to be more conservative in detecting AFib in epochs so as to prevent or reduce the number of false positives that are generated. Feature processor 510 can be configured, e.g., pre-trained, to be more sensitive, e.g., less conservative, in detecting AFib in epochs in view of the higher quality data that is available for such epochs.

Figure 6:
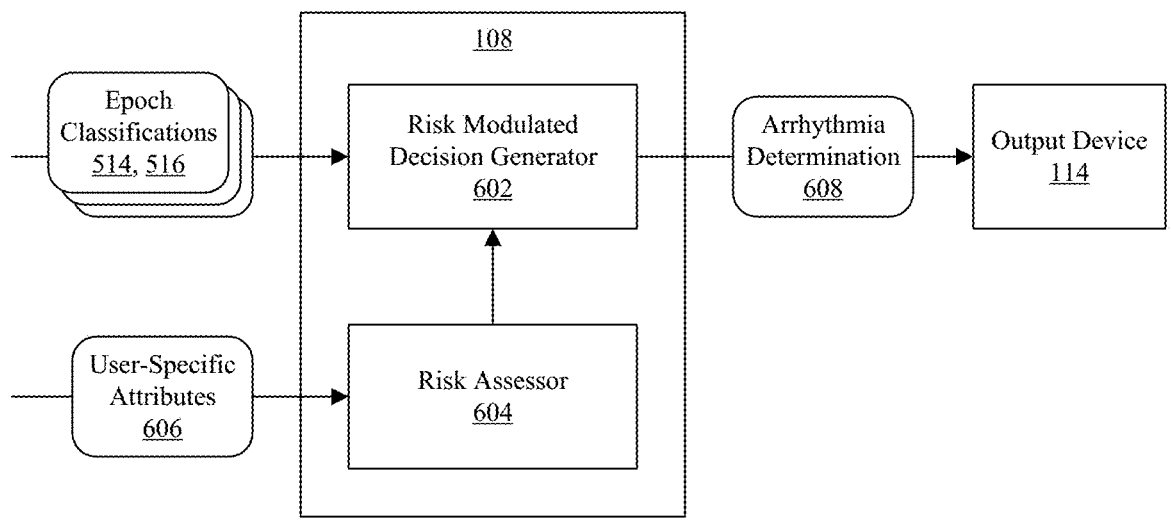
FIG. 6 illustrates an example implementation of a decision generator described in connection with FIG. 1.

FIG. 6 illustrates an example implementation of decision generator 108 of FIG. 1. Decision generator 108 is capable of processing received epochs classifications 514, 516 and, based on epoch classifications 514, 516, make a determination of whether the user is suffering or has suffered from arrhythmia and, more particularly, AFib.

In the example of FIG. 6, decision generator 108 includes a risk-modulated decision generator 602 and a risk assessor 604. In general, risk-modulated decision generator 602 receives epoch classifications 514, 516. For example, risk-modulated decision generator 602 may receive an array of epoch classifications 514, 516. The epoch classifications correspond to continuous heart rhythm for the user. As an illustrative and non-limiting example, the size of the array of epoch classifications may be 5. In an example where each epoch is 1 minute, the array of epoch classifications covers a period of 5 minutes. Still, the example values for epoch length and size of the array are for purposes of illustration and may differ from those provided.

Risk assessor 604 receives one or more user-specific attributes 606 (e.g., a user profile). Risk assessor 604 is capable of determining one or more operating parameters from the received user-specific attributes 606 and providing the operating parameter(s) to risk modulated-decision generator 602. In one aspect, the received operating parameters bias or configure risk-modulated decision generator 602 to generate arrhythmia determination 608 in a manner that accounts for user-specific attributes 606. In an example implementation, user-specific attributes 606 may include, but are not limited to, age of the user, gender of the user, and one or more aspects of the health history of the user. For example, risk assessor 604 is capable of generating threshold scores A and B, where A>B, based on user-specific attributes 606. The threshold scores A and B may be provided to risk-modulated decision generator 602 as the operating parameters.

Figure 7:
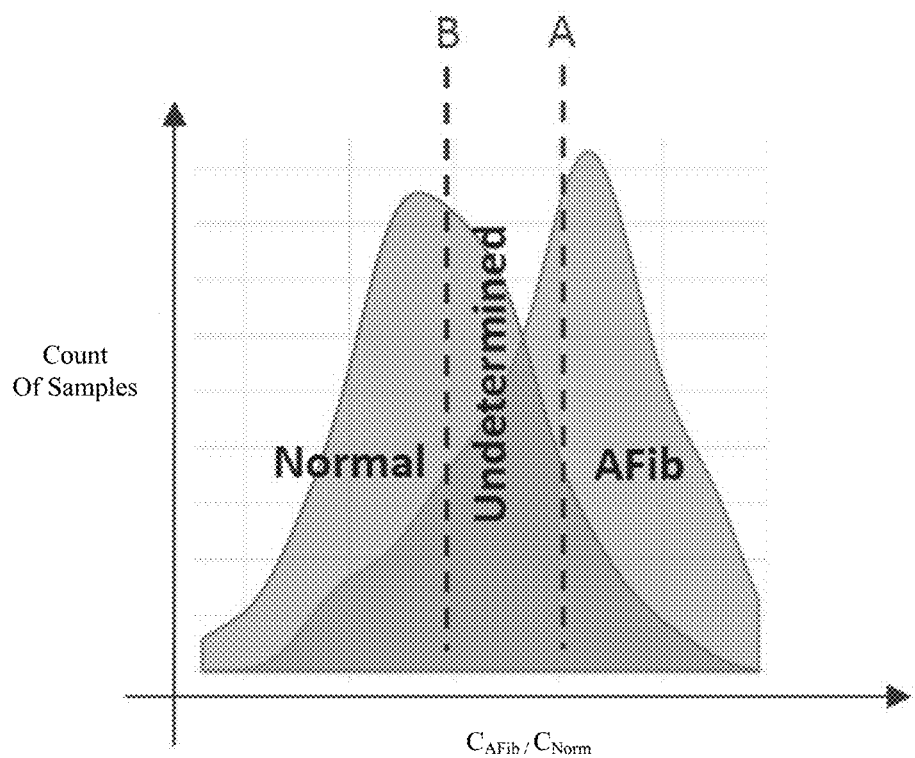
FIG. 7 is a graph illustrating example operating parameters for use with a risk-modulated decision generator described in connection with FIG. 6.

In one aspect, threshold scores A and B may be set to capture risk factors such as age of the user. Risk of AFib increases significantly with age particularly in users over 65 years of age. In an example implementation, scores A and B may be determined using one or more clinical prediction rules that may be mapped onto scores A and B. For instance, scores A and B may be determined using the $CHA_2DS_2$-VASc score where the B score represents the mean of the normal distribution in FIG. 7 while score A represent the mean of the AFib distribution in FIG. 7. User-specific attributes 606 may be those attributes used for the $CHA_2DS_2$-VASc score or other similar instrument. The region between A and B represents an undetermined state where risk-modulated decision generator 602 is unable to make a determination as to whether AFib is detected.

In one aspect, by virtue of configuration via risk assessor 604, risk-modulated decision generator 602 is capable of achieving both a high AFib detection rate for at-risk populations and a low false alarm rate for low-risk populations. Based on the received operating parameters, risk-modulated decision generator 602 is capable of determining whether the user is suffering from AFib based on the array of epoch classifications 514, 516 and the operating parameters received from risk assessor 604. The operating parameters (e.g., scores A and B) configure risk-modulated decision generator 602 to be more conservative in making AFib determinations for users with lower risk of AFib to suppress false positives while being more sensitive in making AFib determinations for users with higher risk of AFib to improve the detection rate.

For example, risk-modulated decision generator 602 is capable of evaluating the previous five consecutive epoch classifications. In the case of an older user, in response to determining that three of the five epochs were classified as indicating AFib, risk-modulated decision generator 602 detects AFib for the user and outputs that determination as arrhythmia determination 608. In the case of a younger user, risk-modulated decision generator 602 may require five out of five epoch classifications indicating AFib to determine that AFib is detected for the user and indicate that decision as arrhythmia determination 608.

Risk-modulated decision generator 602 is capable of making a final decision as to whether the user is suffering from AFib by counting the number of epochs indicating AFib (e.g., "AFib epochs" denoted as $C_{AFib}$) and counting the number of normal epochs (denoted as $C_{norm}$, where a normal epoch is an epoch that does not indicate AFib. The counting and evaluation may be performed for an array of epoch classifications 514, 516 of a predetermined size. In one aspect, the array may be formed using a moving window spanning received epoch classifications over time.

In an example implementation, risk-modulated decision generator 602 is capable of generating arrhythmia determination 608 using the processing rules set forth below for a given array of epoch classifications. Arrhythmia determination 608 is referred to as the "Final Decision" below.

$$\text{Final decision} = AFib \text{ if } \frac{C_{AFib}}{C_{AFib} + C_{norm}} > A; \quad (1)$$

$$\text{Final decision} = \text{Normal if } \frac{C_{AFib}}{C_{AFib} + C_{norm}} < B \quad (2)$$

Final decision = Undetermined if neither rule 1 nor rule 2 is met (3)

In the example of FIG. 6, decision generator 108 is capable of evaluating AFib decisions for smaller time periods (e.g., the epoch classifications) and refining the decisions collectively to balance the amount of data utilized in making arrhythmia determination 608 and the accuracy of such decisions provided to the user. As discussed, arrhythmia determination 608 may be modulated by user-specific attributes 606 for improved accuracy.

In one or more other example implementations, decision generator 108 may determine whether the user has AFib based on received epoch classifications 514 and 516 without including risk assessor and/or using user-specific attributes 606.

Figure 8:
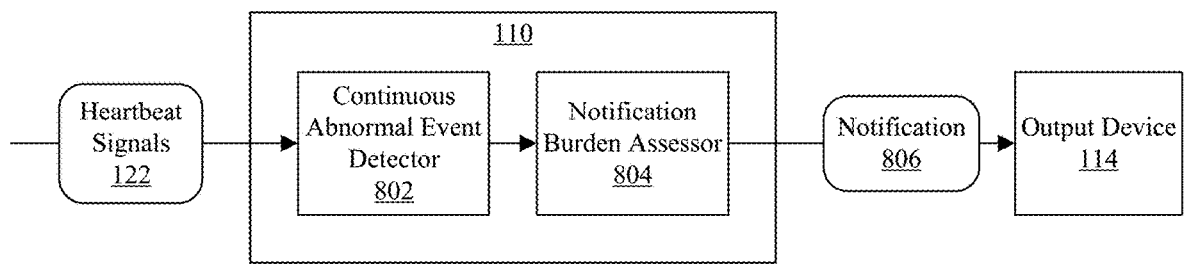
FIG. 8 illustrates an example implementation of a sensor contact monitor described in connection with FIG. 1.

FIG. 8 illustrates an example implementation of sensor contact monitor 110 of FIG. 1. Sensor contact monitor 110 is capable of operating in parallel with the other signal processing blocks described (e.g., IBI generator 104, epoch classification module 106, and decision generator 108). In general, sensor contact monitor 110 is capable of continuously monitoring sensor signals such as heartbeat signals 122 in real-time to detect abnormal events that are characteristic of inappropriate sensor contact (e.g., placement) with the user. Sensor contact monitor 110 is capable of notifying the user of the detected abnormalities and optionally provide instructions as to how to remedy or correct the sensor placement. In an example implementation, sensor contact monitor 110 also is capable of assessing the notification burden imposed on the user and providing notifications only in response to determining that the notification burden on the user is low.

In the example, sensor contact monitor 110 includes a continuous abnormal event detector 802 and a notification burden assessor 804. Continuous abnormal event detector 802 receives sensor signals such as heartbeat signals 122. Continuous abnormal event detector 802 is capable of analyzing heartbeat signals 122 to detect abnormal events therein. Examples of abnormal events that may be detected in heartbeat signals 122 can include, but are not limited to, signal clipping, flattening of the signal, and pauses or interruptions in heartbeat signals 122. In response to detecting abnormal event(s) for a sliding window of time, continuous abnormal event detector 802 is capable of outputting one or more flags indicating detection of such events to notification burden assessor 804.

Notification burden assessor 804 determines the user's notification burden. That is, notification burden assessor 804 is capable of measuring the number of notifications provided to the user over time, including recently provided notifications. In one aspect, notification burden assessor 804 monitors only those notifications generated by sensor contact monitor 110 as opposed to all notifications that may be generated by other applications also executing in electronic device 100. In response to determining that the user's notification burden is low, for example, notification burden assessor 804 outputs notification 806 to output device 116 in response to receiving one or more flags or a minimum number of flags for a given period of time. In response to determining that the user's notification burden is high, notification burden assessor 804 does not pass a notification to output device 116 and continues to monitor flags generated by continuous abnormal event detector 802.

Figure 9:
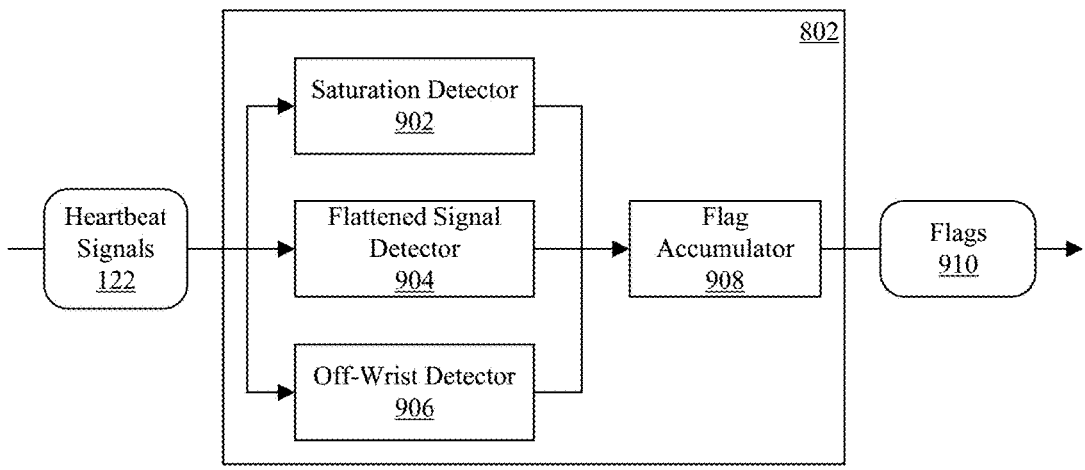
FIG. 9 illustrates an example implementation of a continuous abnormal event detector described in connection with FIG. 8.

FIG. 9 illustrates an example implementation of continuous abnormal event detector 802 of FIG. 8. In the example, continuous abnormal event detector 802 includes a saturation detector 902, a flattened signal detector 904, an off-wrist detector 906, and a flag accumulator 908.

Figure 10:
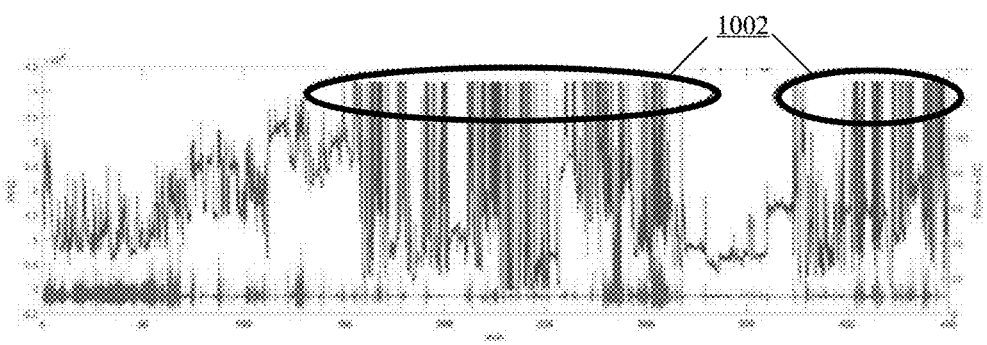
FIG. 10 illustrates an example of clipped heartbeat signals processed by the sensor contact monitor of FIG. 8.

Saturation detector 902 is capable of detecting heartbeat signals 122 exhibiting clipping. FIG. 10 illustrates an example of heartbeat signals 122 with clipping 1002. More particularly, FIG. 10 illustrates an example of clipped PPG signals. In one aspect, saturation detector 902 is capable of asserting or generating a clipping flag to flag accumulator 908 in response to detecting clipping in heartbeat signals 122 that lasts for at least a predetermined amount of time.

Flattened signal detector 904 is capable of detecting heartbeat signals 122 that have a variation that is lower than a predetermined variation threshold. Such signals characteristically have a low signal-to-noise (SNR) ratio. In one aspect, flattened signal detector 904 is capable of asserting or generating a flattened flag to flag accumulator 908 in response to detecting flattening in heartbeat signals 122 that lasts for a predetermined amount of time.

Off-wrist detector 906 is capable of detecting when heartbeat sensor 114 is not in contact with the user. In the case where heartbeat sensor 114 is worn on the user's wrist, e.g., when included in a smart watch, off-wrist detector 906 is capable of detecting that heartbeat sensor 114 is unattached or not in contact with the user's wrist. Off-wrist detector 906 is capable of detecting discontinuities in heartbeat signals 122. Discontinuities are pauses, drop-outs, or the absence of heartbeat signals 122. In one aspect, off-wrist detector 906 is capable of asserting or generating an off-wrist flag to flag accumulator 908 in response to detecting a discontinuity in heartbeat signals 122 that lasts for a predetermined amount of time.

Referring to operation of saturation detector 902, flattened signal detector 904, and off-wrist detector 906, the amount of time that the particular phenomenon is detected by each respective detector before generating a flag may be specific to that detector. That is, saturation detector may use a predetermined minimum amount of time for detecting saturation that differs from the predetermined amount of time to detect flattening and/or off-wrist events (e.g., discontinuities).

Flag accumulator 908 is capable of receiving flags from saturation detector 902, flattened signal detector 904, and/or off-wrist detector 906, and outputting flags 910 to notification burden assessor 804. In one aspect, flags 910 are accumulated for a window of time (e.g., a particular time period such as an epoch).

Figure 11:
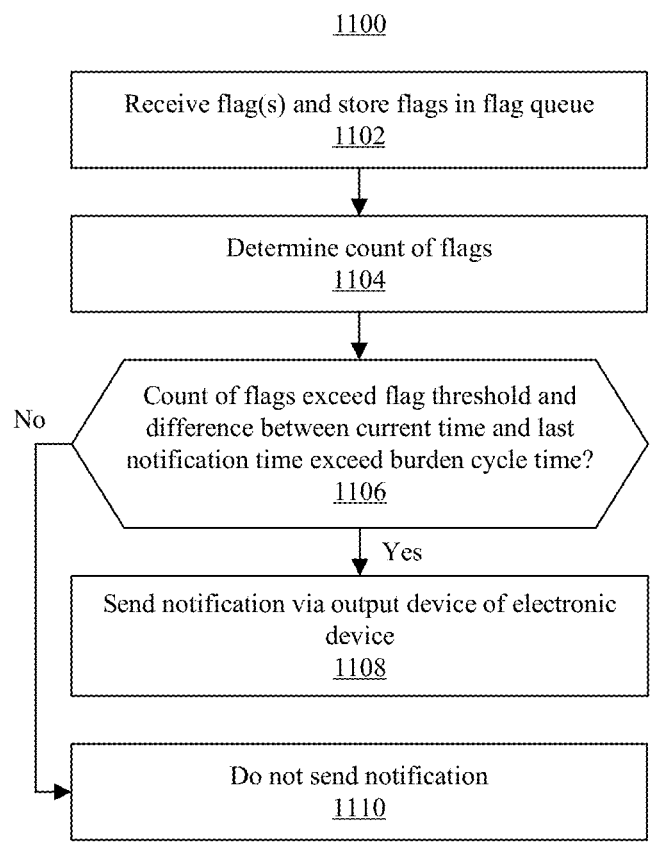
FIG. 11 illustrates an example method of determining notification burden and outputting notifications as performed by a notification burden assessor described in connection with FIG. 8.

FIG. 11 illustrates an example method 1100 of determining notification burden and outputting notifications as performed by notification burden assessor 804 of FIG. 8. In block 1102, notification burden assessor 804 receives flags 910 (e.g., accumulated flags from saturation detector 902, flattened signal detector 904, and/or off-wrist detector 906 for a window of time) and stores the flags in a flag queue therein. In block 1104, notification burden assessor 804 determines a count of the flags stored in the flag queue for the window of time.

In block 1106, notification burden assessor 804 determines whether the count of flags exceeds a threshold count and whether a difference between a current time and the last notification time exceeds a burden cycle time. The threshold count is a predetermined number to which the count of flags is compared. The last notification time is the time that notification 806 was last sent to output device 116 by notification burden assessor 804. Burden cycle time is a predetermined amount of time that may be selected so that the user is not inundated with notifications to fix or adjust sensor(s).

In response to determining that the count of flags exceeds the threshold count and that the difference between the current time and the last notification time exceeds the burden cycle time, notification burden assessor 804 determines that the notification burden on the user is acceptable (e.g., low) and method 1100 continues to block 1108. In response to determining that the count of flags does not exceed the threshold count and/or the difference between the current time and the last notification time does not exceed the burden cycle time, notification burden assessor 804 determines that the notification burden on the user is unacceptable (e.g., high) and method 1100 continues to block 1110.

In block 1108, notification burden assessor 804 sends a notification via output device 116 of electronic device 100. In an example implementation, the content of notification 806 may depend on the type of flag or flags stored in the flag queue and counted as part of the count of flags.

As an illustrative example, in cases where one or more clipping flags are queued, notification burden assessor 804 may include content (e.g., text or other message) in notification 806 asking the user to loosen the strap or mechanism securing heartbeat sensor 114 to alleviate saturation detected in heartbeat signals 122. In another example, in cases where one or more flattened flags are queued, notification burden assessor 804 may include content in notification 806 asking the user to check the strap or mechanism securing heartbeat sensor 114 and possibly tighten the strap or mechanism so that heartbeat sensor 114 makes better contact with the user. In another example, in cases where one or more off-wrist flags are stored in the queue, notification burden assessor 804 may include content in notification 806 asking the user to check the strap or mechanism securing heartbeat sensor 114 and tighten the strap or mechanism so that heartbeat sensor 114 makes better contact with the user.

In block 1110, notification burden assessor 804 does not send a notification.

After blocks 1108 and 1110, method 1100 may continue to iterate to provide timely notifications to the user indicating the occurrence of abnormal events in the sensor data and optionally providing instructions for correcting the placement of the sensors in response to determining that the notification burden is not too high.

FIG. 12 illustrates an example method 1200 of detecting arrhythmia in a user using the example system of FIG. 1. Method 1200 illustrates an example method of continuous heart rhythm monitoring to detect arrhythmia and, more particularly AFib, in a user.

In block 1202, IBI generator 104 is capable of grouping a plurality of IBI data for a user into a plurality of epochs, wherein each epoch includes a subset of the IBI data corresponding to a predetermined time span. As noted, in generating epochs, IBI generator 104 is capable of assessing the quality of IBI data on an individual basis and keeping or discarding each such IBI datum based on the quality assessment. In general, as each epoch represents a fixed time span, each epoch is formed to include the subset of IBI data that occur within the time span represented by the epoch, where those IBI datum or IBI data that were discarded being omitted.

In one aspect, for each IBI datum, in response to determining that an amount of noise in heartbeat signals corresponding in time to the IBI datum exceeds a noise threshold, epoch generator 214 of IBI generator 104 discards the IBI datum such that the IBI datum is not included in an epoch output from IBI generator 104. The noise may be detected by BD 208.

In another aspect, for each IBI datum, in response to determining that an amount of noise in heartbeat signals corresponding in time to the IBI datum does not exceed a noise threshold and an amount of variance in the IBI datum compared to at least one other consecutive IBI datum does not exceed a variance threshold, epoch generator 214 keeps the IBI datum such that the IBI datum is included in an epoch output from IBI generator 104. The variance may be detected by ID 210.

In another aspect, for each IBI datum, in response to determining that an amount of noise in heartbeat signals corresponding in time to the IBI datum does not exceed a noise threshold, an amount of variance in the IBI datum compared to at least one other consecutive IBI datum exceeds a variance threshold, and an amount of motion of electronic device 100 determined from motion sensor data corresponding in time to the IBI datum exceeds a motion threshold, epoch generator 214 discards the IBI datum such that the IBI datum is not included an epoch output from IBI generator 104. Amount of motion may be determined by MA 206.

In another aspect, for each IBI datum, in response to determining that an amount of noise in heartbeat signals corresponding in time to the IBI datum does not exceed a noise threshold, an amount of variance in the IBI datum compared to at least one other consecutive IBI datum exceeds a variance threshold, and an amount of motion of the electronic device determined from motion sensor data corresponding in time to the IBI data does not exceed a motion threshold, epoch generator 214 keeps the IBI datum such that the IBI datum is included in an epoch output from IBI generator 104.

In block 1204, for each of the plurality of epochs, epoch classification module 106 is capable of extracting a selected feature set from the epoch based on a determination of temporal consistency of the epoch. The selected feature set is selected from a plurality of different feature sets. The plurality of feature sets can include a first feature set including both temporal sensitive features and temporal insensitive features. The plurality of feature sets also can include a second feature set including only temporal insensitive features.

In one aspect, temporal evaluator 502 of epoch classification module 106 is capable of determining whether each epoch is temporal consistent based one or more gaps detected in the subset of the IBI data of the epoch. Gaps in the epochs occur in consequence of discarding one or more IBI data during generation of epochs as performed by epoch generator 214.

In block 1206, epoch classification module 106 is capable of generating a plurality of epoch classifications for the plurality of epochs using a selected feature processor. Each epoch classification indicates whether arrhythmia is detected for the corresponding epoch from which the epoch classification is generated. The selected feature processor is selected from a plurality of different feature processors 510, 512 on a per-epoch basis based on the feature set extracted from the epoch. For example, the feature processor used to generate the epoch classifications is specific to the particular feature set extracted from the epoch.

In block 1208, decision generator 108 is capable of outputting, via output device 116 of electronic device 100, an indication of arrhythmia (e.g., arrhythmia determination 608) based on the plurality of epoch classifications. As noted, the indication of arrhythmia may specify that AFib has been detected based on the monitoring of motion signals 112 and heartbeat signals 114. The indication of arrhythmia may be based on the plurality of epoch classifications and further may be determined based on user-specific attributes 606.

In one aspect, the indication of arrhythmia may be an electronic message or notification displayed via a user interface, e.g., a graphical user interface, on a display screen of electronic device 100 indicating that AFib has been detected for the user. In another example, decision generator 108 may generate a notification indicating AFib burden on the user. In other example implementations, the notification provided by electronic device 100 may be conveyed or rendered using another modality such as text-to-speech (e.g., audio) via an audio output device or the like. In still another example, an electronic message indicating that the user experienced AFib and/or indicating AFib burden may be sent from electronic device 100 over a communication network to a destination electronic system. The destination electronic system may be one that is predetermined or otherwise programmed into electronic device 100 such as one that belongs or corresponds to a healthcare provider of the user.

Figure 13:
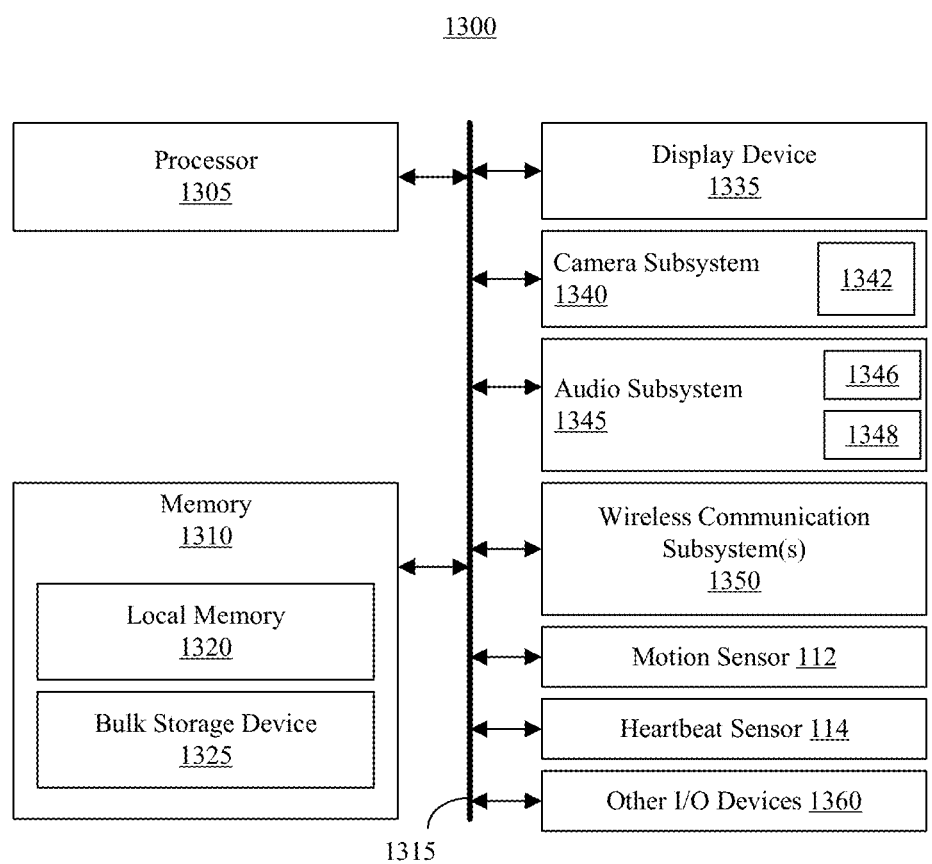
FIG. 13 illustrates an example architecture for an electronic device described in connection with FIG. 1.

FIG. 13 illustrates an example architecture 1300 for electronic device 100 of FIG. 1. Architecture 1300 is an example of computer hardware and includes at least one processor 1305. Processor 1305 is coupled to memory 1310 through interface circuitry 1315. Architecture 1300 stores computer readable program instructions (also referred to as "program code") within memory 1310. Memory 1310 is an example of computer readable storage media. Processor 1305 executes the program code accessed from memory 1310 via interface circuitry 1315.

Processor 1305 is implemented as at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

Memory 1310 includes one or more physical memory devices such as, for example, a local memory 1320 and a bulk storage device 1325. Local memory 1320 is implemented as non-persistent memory device(s) generally used during actual execution of the program code. Examples of local memory 1320 include random access memory (RAM) and/or any of the various types of RAM that are suitable for use by a processor during execution of program code. Bulk storage device 1325 is implemented as a persistent data storage device. Examples of bulk storage device 1325 include a hard disk drive (HDD), a solid-state drive (SSD), flash memory, a read-only memory (ROM), an erasable programmable read-only memory (EPROM), electrically erasable programmable read-only memory (EEPROM), or other suitable memory. Architecture 1300 may also include one or more cache memories (not shown) that provide temporary storage of at least some program code in order to reduce the number of times program code must be retrieved from a bulk storage device during execution.

Examples of interface circuitry 1315 include, but are not limited to, an input/output (I/O) subsystem, an I/O interface, a bus system, and a memory interface. For example, interface circuitry 1315 may be implemented as any of a variety of bus structures and/or combinations of bus structures including a memory bus or memory controller, a peripheral bus, an accelerated graphics port, and a processor or local bus.

In one or more example implementations, processor 1305, memory 1310, and/or interface circuitry 1315 are implemented as separate components. In one or more other example implementations, processor 1305, memory 1310, and/or interface circuitry 1315 are integrated in one or more integrated circuits. The various components in architecture 1300, for example, can be coupled by one or more communication buses or signal lines (e.g., interconnects and/or wires). Memory 1310 and each device therein may be coupled to interface circuitry 1315 via a memory interface, e.g., one or more memory controllers (not shown).

Architecture 1300 may include one or more I/O devices such as a display device 1335, a camera subsystem 1340, and an audio subsystem 1345. Each of display device 1335, camera subsystem 1340, and audio subsystem 1345 is an example of output device 116 of FIG. 1. Display device 1335 may be implemented as a touch-sensitive or touchscreen display capable of receiving touch input from a user. A touch sensitive display and/or a touch-sensitive pad is capable of detecting contact, movement, gestures, and breaks in contact using any of a variety of available touch sensitivity technologies.

Camera subsystem 1340 can be coupled to interface circuitry 1315 directly or through a suitable input/output (I/O) controller. Camera subsystem 1340 can include or be coupled to an optical sensor 1342. Optical sensor 1342 may be implemented using any of a variety of technologies. Examples of optical sensor 1342 can include, but are not limited to, a charged coupled device (CCD) or a complementary metal-oxide semiconductor (CMOS) optical sensor. Camera subsystem 1340 and optical sensor 1342 are capable of performing camera functions such as recording images and/or recording video.

Audio subsystem 1345 can be coupled to interface circuitry 1315 directly or through a suitable input/output (I/O) controller. Audio subsystem 1345 can include or be coupled to a speaker 1346 and a microphone 1348 to facilitate voice-enabled functions, such as voice recognition, voice replication, text-to-speech output of notifications and/or messages, digital recording and/or playback of messages or notifications, and telephony functions.

Architecture 1300 may include one or more wireless communication subsystems 1350. Each of wireless communication subsystem(s) 1350 can be coupled to interface circuitry 1315 directly or through a suitable I/O controller (not shown). Each of wireless communication subsystem(s) 1350 is capable of facilitating communication functions. Examples of wireless communication subsystems 1350 can include, but are not limited to, radio frequency receivers and transmitters, and optical (e.g., infrared) receivers and transmitters. The specific design and implementation of wireless communication subsystem 1350 can depend on the particular type of architecture 1300 implemented and/or the communication network(s) over which architecture 1300 is intended to operate.

As an illustrative and non-limiting example, wireless communication subsystem(s) 1350 may be designed to operate over one or more mobile networks, a WiFi network, a short-range wireless network such as a Bluetooth network, and/or any combination of the foregoing. Wireless communication subsystem(s) 1350 can implement hosting protocols such that architecture 1300 can be configured as a base station for other wireless devices.

Architecture 1300 may include motion sensor 112 and heartbeat sensor 114. As noted, motion sensor 112 may be implemented as an IMU. Examples of heartbeat sensor 114 include, but are not limited to, PPG sensor, an electrocardiogram (ECG) device/sensor, a finger temperature sensor, a skin conductance sensor, and/or a respiration rate sensor. Each of sensors 112, 114 can be coupled to interface circuitry 1315 directly or through a suitable I/O controller (not shown). Architecture may include one or more other types of sensors not illustrated in FIG. 13. Examples of other sensors may include, but are not limited to, a light sensor, a proximity sensor, and a location sensor (e.g., a GPS receiver and/or processor) capable of providing geo-positioning sensor data.

Architecture 1300 further may include one or more other I/O devices 1360 coupled to interface circuitry 1315. Other I/O devices 1360 may be coupled to architecture 1300, e.g., interface circuitry 1315, either directly or through intervening I/O controllers (not shown). Examples of other I/O devices 1360 may include, but are not limited to, a track pad, a keyboard, a pointing device, one or more communication ports (e.g., Universal Serial Bus (USB) ports), a network adapter, and buttons or other physical controls depending on the particular form factor of electronic device 100 in which architecture 1300 is implemented.

A network adapter refers to circuitry that enables architecture 1300 to become coupled to other systems, computer systems, remote printers, and/or remote storage devices through intervening private or public networks. Modems, cable modems, Ethernet interfaces, and wireless transceivers not part of wireless communication subsystem(s) 1350 are examples of different types of network adapters that may be used with architecture 1300. One or more of other I/O devices 1360 may be adapted to control functions of one or more or all of the sensors described including, for example, motion sensor 112 and/or heartbeat sensor 114 and/or any of the various subsystems and/or devices of architecture 1300.

Memory 1310 is capable of storing program code, e.g., instructions, that may be executed by processor 1305. For example, memory 1310 may store an operating system and an application that, when executed, causes processor 1305 to initiate the various operations described within this disclosure. As such, the instructions embodied in memory 1310 may be considered an integrated part of architecture 1300. Further, it should be appreciated that any data and/or program code used, generated, and/or operated upon by architecture 1300 (e.g., processor 1305) are functional data structures that impart functionality when employed as part of architecture 1300.

Architecture 1300 is provided for purposes of illustration and not limitation. An electronic device and/or system configured to perform the operations described herein may have a different architecture than illustrated in FIG. 13. The architecture may be a simplified version of architecture 1300 that includes a memory capable of storing instructions and a processor capable of executing instructions. As noted, sensors such as motion sensor 112 and/or heartbeat sensor 114 may be implemented separately from the electronic device and communicatively linked or coupled thereto. In this regard, architecture 1300 may include fewer components than shown or additional components not illustrated in FIG. 13 depending upon the particular type of electronic device that is implemented. For example, architecture 1300 may include different types of I/O devices and/or subsystems depending on the form factor and/or implementation thereof. Further, one or more of the illustrative components may be incorporated into, or otherwise form a portion of, another component. For example, a processor may include at least some memory.

Architecture 1300 may be implemented as a data processing system, a communication device, or other system that is suitable for storing and/or executing program code. Example implementations of architecture 1300 may include, but are not to limited to, a portable computing device, a mobile device such as a smart phone, a wearable computing device (e.g., a smart watch), or other device.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

The terminology used herein is for the purpose of describing particular implementations only and is not intended to be limiting. Notwithstanding, several definitions that apply throughout this document now will be presented.

As defined herein, the singular forms "a," "an," and "the" are intended to include the plural forms as well, unless the context clearly indicates otherwise.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The different types of memory, as described herein, are examples of a computer readable storage media. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, or the like.

As defined here, a "data structure" is a physical implementation of a data model's organization of data within a physical memory. A data structure is formed of specific electrical or magnetic structural elements in a memory and imposes physical organization on the data stored in the memory as used by an application program executed using a processor.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the term "output" means storing data or signals in physical memory elements, e.g., devices, writing data or signals to a display or other peripheral output device, sending or transmitting data or signals to another system, exporting, or the like.

As defined herein, the term "real-time" means a level of processing responsiveness that a user or system senses as sufficiently immediate for a particular process or determination to be made, or that enables the processor to keep up with some external process.

As defined herein, the term "responsive to" and similar language as described above, e.g., "if," "when," or "upon," mean responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

The term "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

As defined herein, the term "user" means a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions" and "program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowcharts or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method for continuous heart rhythm monitoring, the method comprising:
    grouping, using computer hardware, a plurality of inter-beat intervals (IBI) data for a user into a plurality of epochs, wherein each epoch includes a subset of the IBI data corresponding to a predetermined time span;
    for each of the plurality of epochs, extracting, from the epoch, a selected feature set selected from a plurality of feature sets based on a determination of temporal consistency of the epoch;
    generating a plurality of epoch classifications for the plurality of epochs using a selected feature processor, each epoch classification indicating whether arrhythmia is detected for the epoch from which the epoch classification is generated, wherein the selected feature processor is selected from a plurality of different feature processors on a per-epoch basis based on the selected feature set extracted from the epoch; and
    outputting, via an output device of the computer hardware, an indication of arrhythmia based on the plurality of epoch classifications.

2. The method of claim 1, wherein the plurality of feature sets include:
    a first feature set including temporal sensitive features and temporal insensitive features; and
    a second feature set including only temporal insensitive features.

3. The method of claim 1, further comprising:
    determining whether the epoch is temporal consistent based on detecting one or more gaps in the subset of the IBI data of the epoch.

4. The method of claim 1, further comprising:
    for each IBI datum, in response to determining that an amount of noise in heartbeat signals corresponding in time to the IBI datum exceeds a noise threshold, discarding the IBI datum.

5. The method of claim 1, further comprising:
    for each IBI datum, in response to determining that an amount of noise in heartbeat signals corresponding in time to the IBI datum does not exceed a noise threshold and an amount of variance in the IBI datum compared to at least one other consecutive IBI datum does not exceed a variance threshold, keeping the IBI datum for epoch formation.

6. The method of claim 1, further comprising:
    for each IBI datum, in response to determining that an amount of noise in heartbeat signals corresponding in time to the IBI datum does not exceed a noise threshold, an amount of variance in the IBI datum compared to at least one other consecutive IBI datum exceeds a variance threshold, and an amount of motion determined from motion signals corresponding in time to the IBI datum exceeds a motion threshold, discarding the IBI datum.

7. The method of claim 1, further comprising:
    for each IBI datum, in response to determining that an amount of noise in heartbeat signals corresponding in time to the IBI datum does not exceed a noise threshold, an amount of variance in the IBI datum compared to at least one other consecutive IBI datum exceeds a variance threshold, and an amount of motion determined from motion signals corresponding in time to the IBI datum does not exceed a motion threshold, keeping the IBI datum for epoch formation.

8. The method of claim 1, wherein the indication of arrhythmia is determined based on one or more user-specific attributes.

9. A system for continuous heart rhythm monitoring, comprising:
    a processor programmed to initiate operations, the operations including:
        grouping a plurality of inter-beat intervals (IBI) data for a user into a plurality of epochs, wherein each epoch includes a subset of the IBI data corresponding to a predetermined time span;
        for each of the plurality of epochs, extracting, from the epoch, a selected feature set selected from a plurality of feature sets based on a determination of temporal consistency of the epoch;
        generating a plurality of epoch classifications for the plurality of epochs using a selected feature processor, each epoch classification indicating whether arrhythmia is detected for the epoch from which the epoch classification is generated, wherein the selected feature processor is selected from a plurality of different feature processors on a per-epoch basis based on the selected feature set extracted from the epoch; and
        outputting, via an output device of the system, an indication of arrhythmia based on the plurality of epoch classifications.

10. The system of claim 9, wherein the plurality of feature sets include:
   a first feature set including temporal sensitive features and temporal insensitive features; and
   a second feature set including only temporal insensitive features.

11. The system of claim 9, wherein the processor is programmed to initiate operations further comprising:
   determining whether the epoch is temporal consistent based on detecting one or more gaps in the subset of the IBI data of the epoch.

12. The system of claim 9, wherein the processor is programmed to initiate operations further comprising:
   for each IBI datum, in response to determining that an amount of noise in heartbeat signals corresponding in time to the IBI datum exceeds a noise threshold, discarding the IBI datum.

13. The system of claim 9, wherein the processor is programmed to initiate operations further comprising:
   for each IBI datum, in response to determining that an amount of noise in heartbeat signals corresponding in time to the IBI datum does not exceed a noise threshold and an amount of variance in the IBI datum compared to at least one other consecutive IBI datum does not exceed a variance threshold, keeping the IBI datum for epoch formation.

14. The system of claim 9, wherein the processor is programmed to initiate operations further comprising:
   for each IBI datum, in response to determining that an amount of noise in heartbeat signals corresponding in time to the IBI datum does not exceed a noise threshold, an amount of variance in the IBI datum compared to at least one other consecutive IBI datum exceeds a variance threshold, and an amount of motion determined from motion signals corresponding in time to the IBI datum exceeds a motion threshold, discarding the IBI datum.

15. The system of claim 9, wherein the processor is programmed to initiate operations further comprising:
   for each IBI datum, in response to determining that an amount of noise in heartbeat signals corresponding in time to the IBI datum does not exceed a noise threshold, an amount of variance in the IBI datum compared to at least one other consecutive IBI datum exceeds a variance threshold, and an amount of motion determined from motion signals corresponding in time to the IBI datum does not exceed a motion threshold, keeping the IBI datum for epoch formation.

16. The system of claim 9, wherein the indication of arrhythmia is determined based on one or more user-specific attributes.

17. A computer program product, comprising:
   one or more computer readable storage media, and program instructions collectively stored on the one or more computer readable storage media, wherein the program instructions are executable by computer hardware to initiate operations including:
   grouping a plurality of inter-beat intervals (IBI) data for a user into a plurality of epochs, wherein each epoch includes a subset of the IBI data corresponding to a predetermined time span;
   for each of the plurality of epochs, extracting, from the epoch, a selected feature set selected from a plurality of feature sets based on a determination of temporal consistency of the epoch;
   generating a plurality of epoch classifications for the plurality of epochs using a selected feature processor, each epoch classification indicating whether arrhythmia is detected for the epoch from which the epoch classification is generated, wherein the selected feature processor is selected from a plurality of different feature processors on a per-epoch basis based on the selected feature set extracted from the epoch; and
   outputting, via an output device of the computer hardware, an indication of arrhythmia based on the plurality of epoch classifications.

18. The computer program product of claim 17, wherein the plurality of feature sets include:
   a first feature set including temporal sensitive features and temporal insensitive features; and
   a second feature set including only temporal insensitive features.

19. The computer program product of claim 17, wherein the program instructions are executable by the computer hardware to initiate operations further comprising:
   for each IBI datum, in response to determining that an amount of noise in heartbeat signals corresponding in time to the IBI datum does not exceed a noise threshold and an amount of variance in the IBI datum compared to at least one other consecutive IBI datum does not exceed a variance threshold, keeping the IBI datum for epoch formation.

20. The computer program product of claim 17, wherein the program instructions are executable by the computer hardware to initiate operations further comprising:
   for each IBI datum, in response to determining that an amount of noise in heartbeat signals corresponding in time to the IBI datum does not exceed a noise threshold, an amount of variance in the IBI datum compared to at least one other consecutive IBI datum exceeds a variance threshold, and an amount of motion determined from motion signals corresponding in time to the IBI datum does not exceed a motion threshold, keeping the IBI datum for epoch formation.

\* \* \* \* \*